US006605285B2

(12) United States Patent
Sharma et al.

(10) Patent No.: US 6,605,285 B2
(45) Date of Patent: Aug. 12, 2003

(54) VACCINE FOR PROTECTION OF POULTRY AGAINST SALMONELLOSIS AND A PROCESS FOR PREPARING THE SAME

(75) Inventors: Vishwashwar Dutt Sharma, Pantnagar (IN); Subodh Kumar, Pantnagar (IN); Shri Krishna Garg, Pantnagar (IN); Ram Sagar Mishra, Khuthan (IN); Tarani Kanta Barman, Kaithalkuchi (IN)

(73) Assignee: G.B. Pant University of Agriculture & Technology, U.P. (IN)

(*) Notice: Subject to any disclaimer, the term of this patent is extended or adjusted under 35 U.S.C. 154(b) by 21 days.

(21) Appl. No.: 09/810,950

(22) Filed: Mar. 19, 2001

(65) Prior Publication Data

US 2003/0124709 A1 Jul. 3, 2003

(30) Foreign Application Priority Data

Mar. 29, 2000 (IN) .................................... 351/DEL/2000
Mar. 29, 2000 (IN) .................................... 352/DEL/2000
Mar. 1, 2001 (IN) .................................... 241/DEL/2001

(51) Int. Cl.[7] ....................... A61K 39/02; A61K 39/112

(52) U.S. Cl. ................................ 424/236.1; 424/258.1; 424/282.1; 530/402; 530/403

(58) Field of Search ................................ 435/252.1, 72, 435/71.3; 424/278.1, 184.1, 203.1, 234.1, 258.1, 282.1, 236.1; 530/402, 403, 825

(56) References Cited

U.S. PATENT DOCUMENTS 4,503,036 A 3/1985 Girardon et al.
5,057,540 A * 10/1991 Kensil et al.
5,080,896 A * 1/1992 Visser et al.

FOREIGN PATENT DOCUMENTS

WO WO 91/06317 5/1991 ......... A61K/39/112
WO WO97/18225 5/1997 ........... C07H/19/00

OTHER PUBLICATIONS

Rahman et al. (Zentralbl Bakteriol 1995 vol. 282(4) pp 416–24; Abstract Only).*

Ashkenazi et al (Infect Immun 1988 vol. 56(12) pp. 3089–3094).*

Rahman, H. and Sharma, V.D. "Immunogenicity and Antigenic Relationhip of Salmonella Enterotoxin with other Enterotoxins." Zentralbl Bakteriol. Oct. 1995; 282(4):416–26. (Complete document).

C. Wray, a Guest Editorial on Salmonellosis: A hundred years old and still going Strong, (1995) Proc. of British Veterinary Journal, 151,4, p. 339–340.

A.J. Lax, P.A. Barrow, P.W. Jones and T.S. Wallis, a Review on Current Perspectives in Salmonellosis, (1995) Proc. of British Veterinary Journal, 151,4, p. 351–377.

B.R.Sngh and V.D. Sharma, Isolation and Chracterization of Four Distinct Cytotoxic Factors of *Salmonella* Weltevreden, (1999) Zent.b.Bakteriol.289, p. 457–474.

* cited by examiner

*Primary Examiner*—Patricia A. Duffy
(74) *Attorney, Agent, or Firm*—Sidley Austin Brown & Wood LLP

(57) ABSTRACT

This invention relates to a process for the preparation of Salmonella vaccine by treating entrotoxin and cytotoxins with formalin and adding immuno-potentiator selected from Freund's complete adjuvant (FCA) or Vitamin E or Saponin to said concentrated toxoids to get the desired vaccine.

Figure 1:
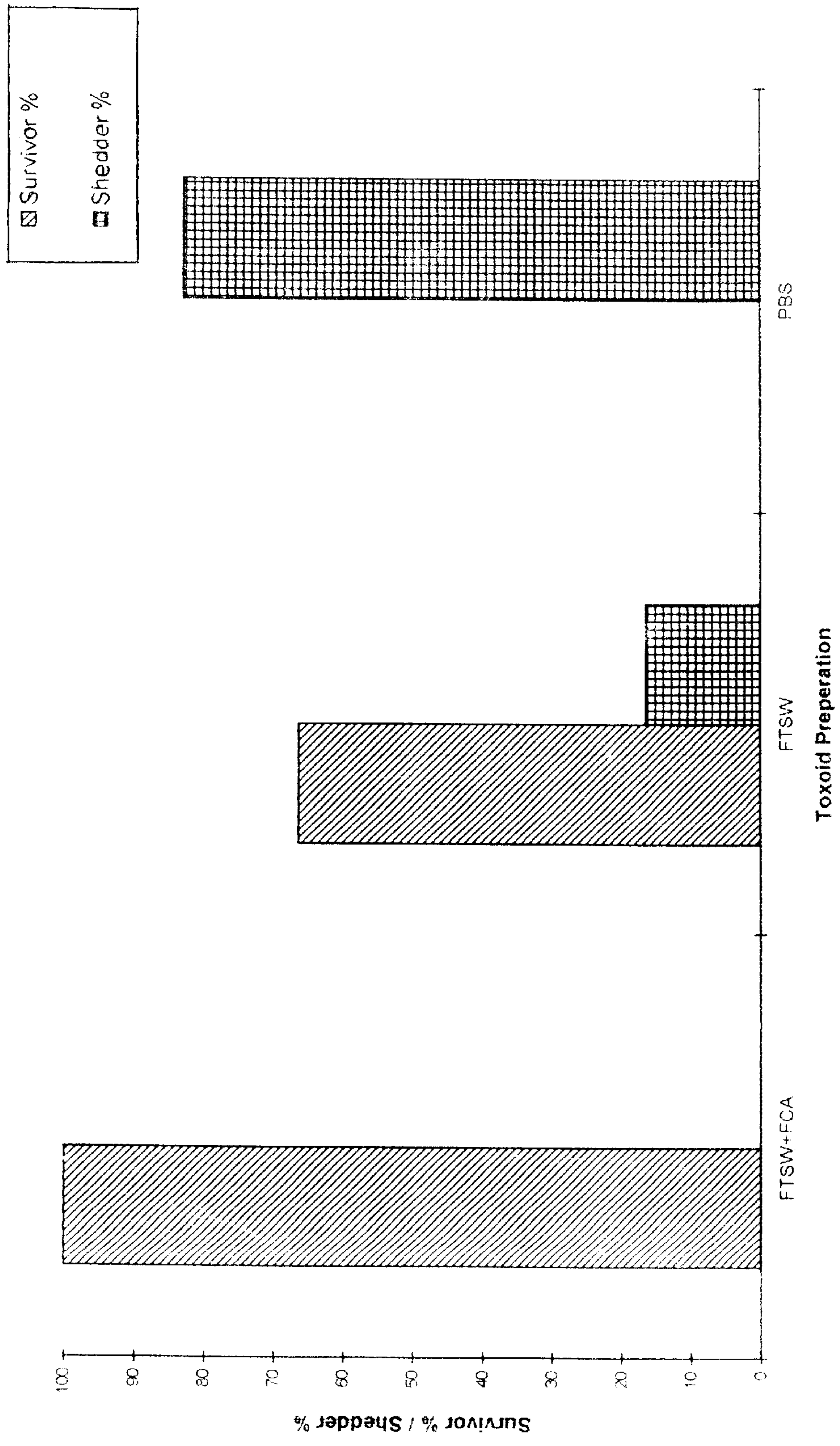

The present invention also provides a Salmonella vaccine for protection against Salmonellosis in poultry.

22 Claims, 4 Drawing Sheets

IMMUNITY CONFERRED BY TOXOID PREPARATIONS

PASSIVE TRANSFER OF IMMUNITY

PROTECTIVE EFFICACY OF SAPONIN ADJUVANTED TOXOID

VACCINE FOR PROTECTION OF POULTRY AGAINST SALMONELLOSIS AND A PROCESS FOR PREPARING THE SAME

BACKGROUND

Salmonellosis remains an important human and animal problem worldwide. In spite of intensive research efforts, many of the details of its pathogenesis are not known. Despite a lack of precise knowledge on the virulence mechanisms of Salmonella, vaccines of varying efficacy have been used for many years (Wray, 1995). Lax, et al (1995) have reviewed the efficiency of different vaccines against salmonellosis. According to them, the efficacy of both live attenuated and dead vaccines remains unclear. Since vaccines developed so far have not been targeted against the virulence factor(s) playing a key role in the pathogenesis of the disease, they may not have for this reason been optimally effective. Moreover, their efficacy have been limited to homologous or antigenically related serovars as Salmonella serovars differ significantly in their flagellar and somatic antigens.

U.S. Pat. No. 4,053,036 also describes a bacterial vaccine against Salmonella fevers, typhoid and paratyphoid fevers. The said vaccine is obtained by fermentation, extraction and purification, vaccinating membrane antigens being extracted by putting the bacterial residue obtained by centrifuging, in contact with a solvent of the tris(hydroxyalkyl) aminoalkane class, with stirring at lower temperature, pH adjusted between 8.4 and 8.6 for a period of at least 60 hours, then separated by decanting, followed by purifying the antigens and fractionating by ultra-filtration and then freeze drying the vaccinating antigen fraction. This patent does not disclose the nature of antigen and whether it has got any role in the pathogenesis of salmonellosis.

International application no. WO 91/06317, filed on 2$^{nd}$ November 1990, discloses vaccines for treatment of individuals for infections by gram negative bacteria. The vaccine consists of a live avirulent Salmonella, which is able to induce immunity to homologous and hetrogenous Salmonella serotypes and two other gram negative bacteria. The vaccine described in the international application has limited use in respect of heterologous Salmonella serotypes and is not targeted against the main virulence factor (toxins).

International application no. WO 97/18225, filed on 14$^{th}$ November 1996, describes substantially pure Salmonella secreted proteins (Ssp), the secretion of which is dependent upon the expression of PrgH; methods of diagnosing Salmonella infection; and live attenuated vaccine strains in which Ssp secretion is decreased. This vaccine also has limited use in respect of heterologous Salmonella serotypes and is not targeted against the main virulence factor (toxins).

The vaccine described in international application nos. WO91/06317 & WO 97/18225 have been prepared using bacterial cells and not from their toxins which play significant role in the pathogenesis of the disease.

Recently, four distinct cytotoxins and an enterotoxin have been isolated from a single strain of *Salmonella enterica* subsp enterica ser Weltevreden (S.Weltevreden) purified to homogeneity and well characterized. These toxins in concert induced clinical changes in experimental animals similar to that observed in natural cases of Salmonellosis suggesting a major role for these toxins in the pathogenesis of the disease. These toxins lost their toxicity on formalin and carbonate treatments but retained their immunogenicity. Singh and Sharma (1999), have published the above findings in Zent. bl. Bakteriol (International Journal of Medical Microbiology).

The object of this invention is to prepare a safe and potent Salmonella vaccine for protection of poultry against salmonellosis.

To achieve the said objective this invention provides a process for the preparation of a vaccine from enterotoxin and cytotoxins isolated from Salmonella sps. for protection against Salmonellosis in poultry, comprising:

treating the said toxins with formalin in the predetermined ratio depending upon the concentration of the formalin and incubating for 40–50 hours at 35–38° C. temperature, removing formalin by dialysis against phosphate buffer saline (PBS), concentrating the formalized toxoid by dialysing against polyethylene glycol, and adding immuno-potentiator selected from Freund's complete adjuvant (FCA) or Vitamin E or Saponin, to said concentrated formalized toxoids to get the desired vaccine.

The said enterotoxin and cytotoxins is isolated from a single strain of S.Weltevreden, *S. typhimrium* and *S. gallinarum.*

The said enterotoxin and cytotoxins is isolated from a single strain of S.Weltevreden.

The concentration of formalin is 0.1–0.25%, preferably 0.2%.

The ratio of the concentration of formalin with toxin is 1:1

The pH concentration of phosphate buffer saline (PBS) is 7.4.

The said polyethylene glycol is 30% polyethylene glycol-20,000.

The concentration of said formalized toxoid is 0.1 mg/ml.

The amount of said FCA is 0.5–1 ml of the said concentrated toxoid, preferably 1 ml/ml.

The amount of said vitamin E is 90–110 international units (IU) of the said concentrated toxoid, preferably 100 IU/ml.

The amount of said saponin is 50–150 $\mu$g of the said concentrated toxoid.

The amount of said saponin is preferably 100 $\mu$g of the said concentrated toxoid.

The present invention also provides a Salmonella vaccine whenever prepared by above process for protection against Salmonellosis in poultry, wherein said vaccine affords protection against homologous (S.Weltevreden) as well as against heterologous (*S. typhimrium* and *S. gallinarum*) serovars.

The said vaccine affords protection against homologous (S.Weltevreden) serovars. The invention will now be described with reference to the following examples and accompanying drawings:

EXAMPLE 1

The toxins (enterotoxin and cytotoxins) were treated with 0.2% formalin in the ratio 1:1 and incubating for 48 hours at temperature 37° C. Removing formalin by dialysis against phosphate buffer saline (PBS, pH 7.4) and concentrating the formalized toxins to original protein concentration by dialysing against 30% polyethylene glycol -20,000. Adding 1 ml FCA to the said concentrated toxoid to get the desired vaccine.

The above vaccine was tested for its efficacy in poultry and the following tests were performed:

21-day-old chicks were vaccinated with the above vaccine @2 ml per bird subcutaneously. The vaccinated birds were challenged intraperitoneally with Salmonella Weltevreden, *Salmonella gallinarum* and *S. typhimurium* separately @2×$10^9$ CFU/bird at 15 days post vaccination. The birds were checked for protection and immune-response as given in table 1.

In table 1 and FIG. 1, the comparative efficacy of the vaccine against experimental salmonellosis in poultry has been presented. It may be seen from table 1 that the vaccine is effective and afforded 100% protection against homologous (Salmonella Weltevreden), as well as against heterologous (*Salmonella gallinarum* and *S. typhimurium*) serovars. No untoward reaction was noticed in the vaccinated birds. This indicates that the vaccine is safe and potent.

Furthermore, the vaccine also checked shedding of the challenged organism by the vaccinated birds in their faeces. It may be seen that with this vaccine, shedding of the organism by the vaccinated birds is nil, whereas in the control group all the surviving birds shed the organism. This is important from public health point of view, as the shedders act as carriers and contribute significantly to the spread of the organism.

TABLE 1

Immunoprophylactic efficacy of Salmonella Toxoid

| SL. NO. | IMMUNIZED WITH | AGGLUTI-NATION TITRE | ELISA TITRE | SUB-GROUPS* | CHALLENGE ORGANISM ($2 \times 10^6$ CFU) | SURVIVOR PERCENTAGE | SHEDDER PERCENTAGE |
|---|---|---|---|---|---|---|---|
| 1 | FTSW + FCA | 1365 ± 216** | $5.5 \times 10^6 \pm 2 \times 10^6$** | A1 | S.W. | 100.00 | 0.00 |
| | | | | A2 | S.G. | 100.00 | 0.00 |
| | | | | A3 | S.T. | 100.00 | 0.00 |
| 2 | FTSW | 853 ± 108 | $4 \times 10^5 \pm 1.5 \times 10^5$ | B1 | S.W. | 66.66 | 16.66 |
| | | | | B2 | S.G. | 58.33 | 33.33 |
| | | | | B3 | S.T. | 58.33 | 33.33 |
| 3 | PBS | 5 ± 1 | $4 \times 10^1 \pm 1.8 \times 10^1$ | C1 | S.W. | NIL | 83.33 |
| | | | | C2 | S.G. | 16.66 | 75.00 |
| | | | | C3 | S.T. | NIL | 83.00 |

*Each group contains 36 chicken and each subgroup 12 chicken
**Mean ± S.E.
S.W. = *Salmonella enterica* subsp *enterica* ser Weltevreden (S. Weltevreden)
S.T. = S. ser Typhimurium
S.G. = S. ser Gallinarum
FTSW = Formalin treated *S. enterica* ser Weltevreden Toxoid
PBS = Phosphate Buffer Saline
FCA = Freund's Complete Adjuvant

EXAMPLE 2

Treating toxins (enterotoxin and cytotoxins), isolated from a single strain of S.Weltevreden, with 0.2% formalin in the ratio 1:1 and incubating for 48 hours at temperature 37° C. Removing formalin by dialysis against phosphate buffer saline (PBS, pH 7.4) and concentrating the formalized toxins to original protein concentration by dialysing against 30% polyethylene glycol -20,000. Adding 100 international unit (IU) of vitamin E to the said concentrated toxoid to get the desired vaccine.

The above vaccine was tested for its efficacy in poultry and the following tests were performed:

21-day-old chicks were vaccinated with the above vaccine @1 ml per bird subcutaneously. The vaccinated birds were challenged intraperitoneally with Salmonella Weltevreden and *Salmonella gallinarum* separately @2×$10^9$ CFU/bird at different intervals, i.e. 30, 60, 120 days post vaccination. The birds were checked for protection and immune-response as given in table 2.

Figure 2:
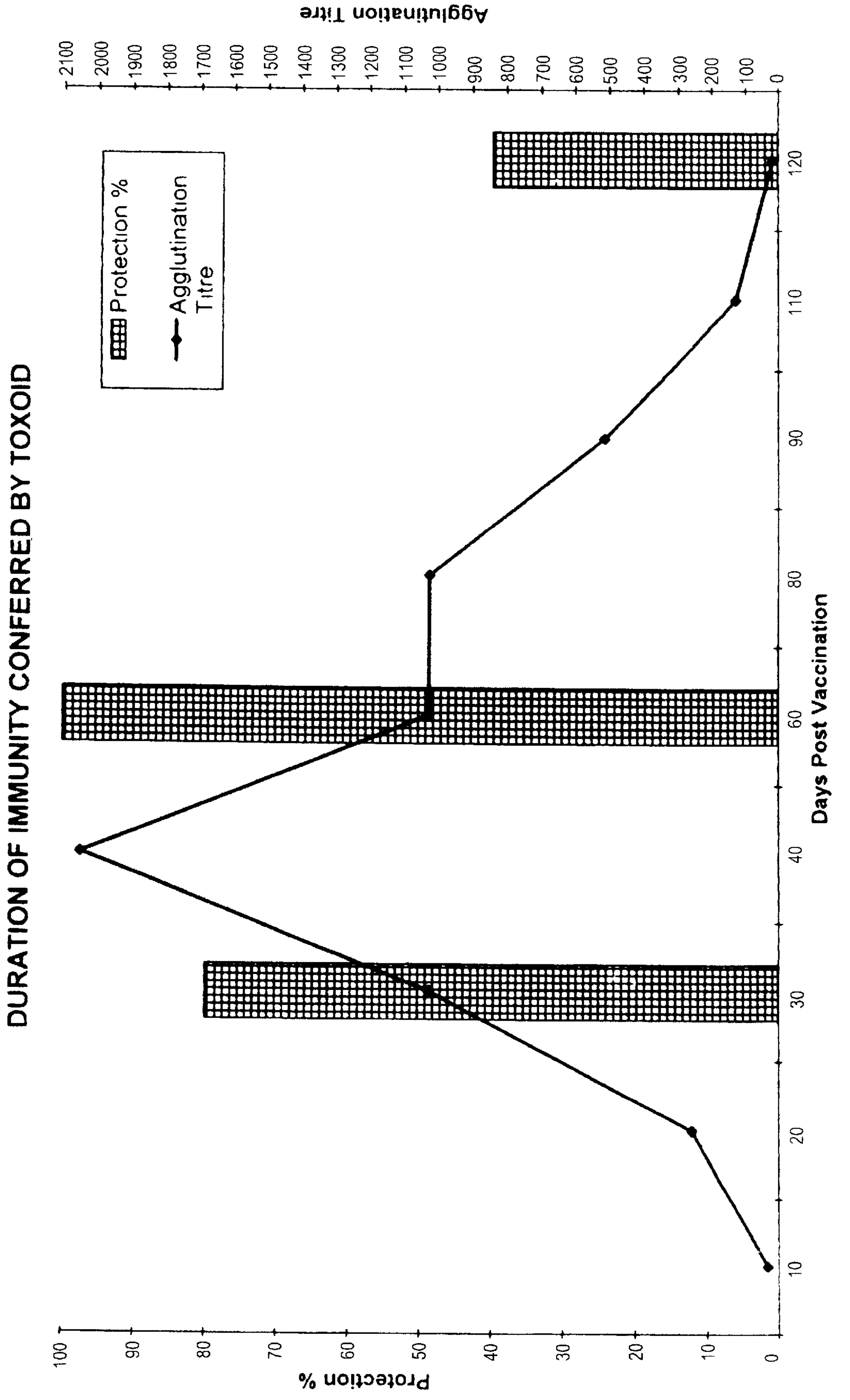

It may be seen from table 2 that the protection available at 30 days is 90% and at 60 days it is 100% and then the protection decreases with the increase of number of days. At 120 days the protection is 40%. This is also evident in the graph given in FIG. 2. It may also be seen that maximum immune-response is found at 40 days and thereafter it starts declining.

In table 3, the comparative efficacy of the vaccine against experimental Salmonellosis in poultry has been presented. It may be seen that the vaccine is effective against homologous (Salmonella Weltevreden), as well as against heterologous (*Salmonella gallinarum*) serovars.

No untoward reaction was observed in the vaccinated birds. This indicates that the vaccine is potent and safe.

Furthermore, the vaccine also checked shedding of the challenged organism by the vaccinated birds in their faeces. It may be seen that with this vaccine, shedding of the organism by the vaccinated birds is nil on 10 days post challenge, whereas in the control group majority of the surviving birds shed the organism. This is important from public health point of view, as the shedders contribute significantly to the spread of the organism.

Figure 3:
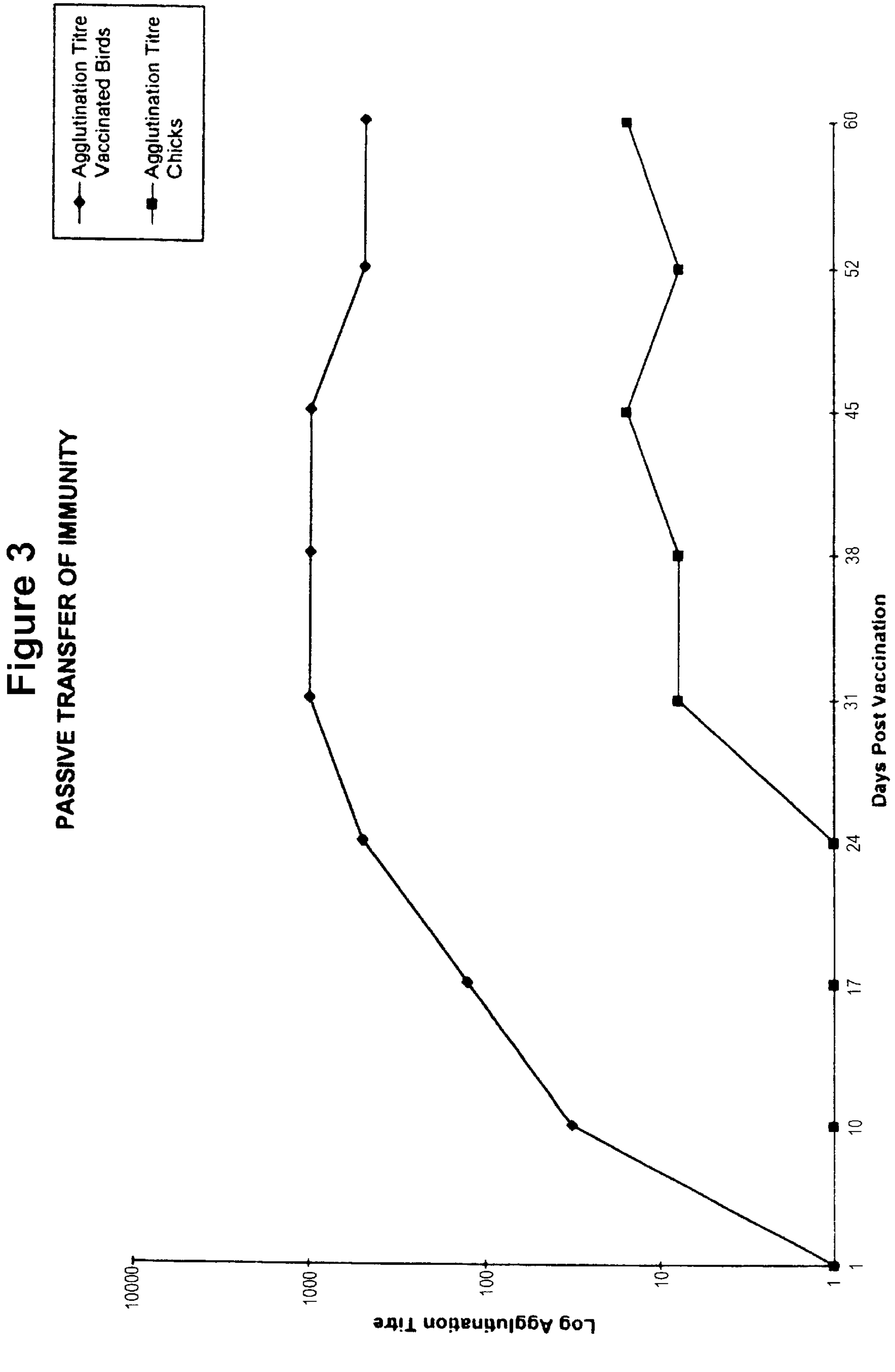

In table 4 and FIG. 3, passive transfer of immunity by the vaccinated birds through eggs has been depicted. It may be inferred from the said table that the immunity in chicks of the vaccinated birds was observed after 24 days of vaccination and continued up to 60 days post vaccination. This is important in protecting chicks in their early life against salmonellosis.

TABLE 2

Duration of immunity conferred by vita E adjuvanted toxoid

| DPV | Agglutination titre | ELISA titre | % survival after challenge with S. Weltevreden |
|---|---|---|---|
| 10 | 32 | $1.1 \times 10^4$ | |
| 20 | 256 | $8.9 \times 10^4$ | |
| 30 | 1024 | $5.1 \times 10^6$ | 90% |
| 40 | 2048 | $3.1 \times 10^7$ | |
| 60 | 1024 | $6.2 \times 10^6$ | 100% |
| 80 | 1024 | $4.9 \times 10^6$ | |
| 90 | 512 | $2.1 \times 10^5$ | |
| 110 | 128 | $6.1 \times 10^3$ | |
| 120 | 16 | $2.1 \times 10^2$ | 40% |

DPV: Days post vaccination

TABLE 3

Comparative efficacy of vita E adjuvanted toxoid against experimental salmonellosis in poultry

| Preparation used for vaccination | Challenge organisn: ($2 \times 10^9$ CFU) | Birds challenged | Shedders/Survivors on different days of cloacal swabs culture | | | | | Protection % |
|---|---|---|---|---|---|---|---|---|
| | | | 2 | 5 | 10 | 15 | 20 | |
| Control (PBS) | SW | 10 | 9/10 | 6/6 | 3/3 | 1/1 | — | 0 |
| | SG | 10 | 8/10 | 8/8 | 2/2 | — | — | 0 |
| Toxoid + | SW | 10 | 0/10 | 0/10 | 0/9 | 0/9 | 0/9 | 90 |
| Vita E | SG | 10 | 2/10 | 1/9 | 1/9 | 0/8 | 0/8 | 80 |
| Toxoid | SW | 10 | 3/10 | 2/9 | 3/9 | 2/8 | 0/6 | 60 |
| | SG | 10 | 4/10 | 3/9 | 2/8 | 0/6 | 0/6 | 60 |
| Vita E | SW | 10 | 8/10 | 6/6 | 2/3 | 2/3 | 0/1 | 10 |
| | SG | 10 | 10/10 | 6/8 | 3/3 | 1/2 | 0/1 | 10 |

SW: S. Weltevreden
SG: S. Gallimarum
PBS: Phosphate buffer saline

TABLE 4

Passive transfer of immunity after vaccination with vita E + toxoid vaccine

| | Agglutination titre | | | |
|---|---|---|---|---|
| Days post vaccination | Vaccinated birds | Unvaccinated birds | Chicks from vaccinated birds | Chicks from unvaccinated birds |
| 10 | 32 | 4 | — | — |
| 17 | 128 | 4 | — | — |
| 24 | 512 | 8 | — | — |
| 31 | 1024 | 4 | 8 | — |
| 38 | 1024 | 8 | 8 | — |
| 45 | 1024 | 8 | 16 | — |
| 52 | 512 | 4 | 8 | — |
| 60 | 512 | 8 | 16 | — |

EXAMPLE 3

Treating toxins (enterotoxin and cytotoxins), isolated from a single strain of S.Weltevreden, with 0.2% formalin in the ratio 1:1 and incubating for 48 hours at temperature 37° C. Removing formalin by dialysis against phosphate buffer saline (PBS, pH 7.4) and concentrating the formalized toxins to original protein concentration by dialysing against 30% polyethylene glycol -20,000. Adding 100 µg Saponin to said concentrated toxoid to get the desired vaccine.

The above vaccine was tested for its efficacy in poultry and the following tests were performed:

21-day-old chicks were vaccinated with the above vaccine @1 ml per bird subcutaneously. The vaccinated birds were challenged intraperitoneally with Salmonella Weltevreden and *Salmonella gallinarum* separately @$2 \times 10^9$ CFU/bird at 21 day post vaccination. The birds were checked for protection and immune-response as given in table 5.

Figure 4:
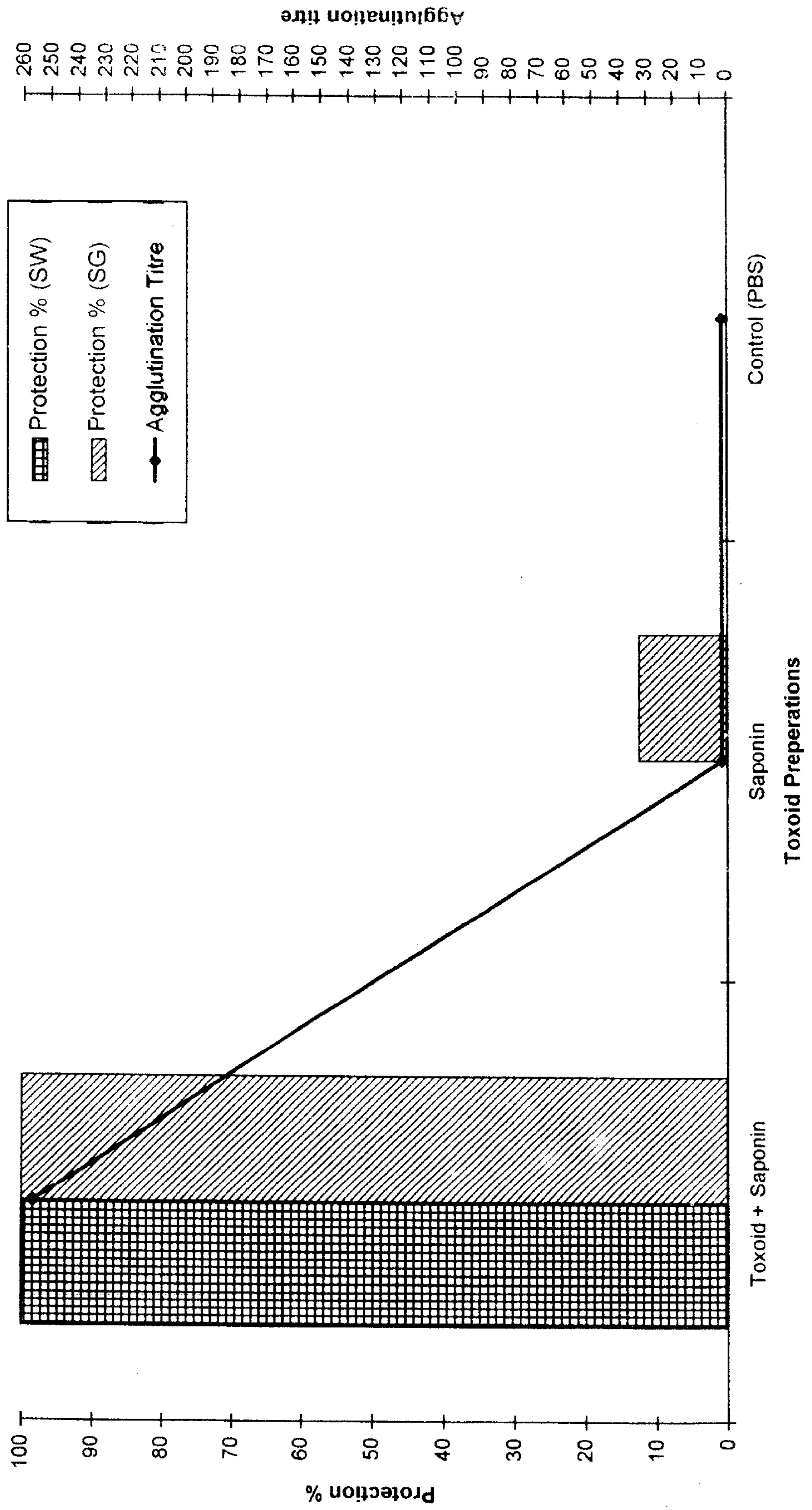

It may be seen from table 5 & FIG. 4 that the protection available at 21 day post vaccination is 100% against both S. Weltevreden and *S. gallinarum* challenge, whereas saponin alone could not afford protection.

In table 6 read with FIG. 4, the humoral immune response to the vaccine assessed by Agglutination test and ELISA has been presented. It may be seen that the vaccine induces significant immune response both in terms of agglutination and ELISA titers. The immune response to Saponin alone was negligible.

No untoward reaction was observed in the vaccinated birds. This indicates that the vaccine is potent and safe.

Furthermore, the vaccine also checked shedding of the challenged organism by the vaccinated birds in their faeces. It may be seen (table 7) that with this vaccine, shedding of the organism by the vaccinated birds is nil on 10 days post challenge, whereas in the control group majority of the surviving birds shed the organism. This is important from public health point of view, as the shedders contribute significantly to the spread of the organism.

TABLE 5

Protection in birds immunized with Saponin adjuvanted toxoid

| Protection in birds immunized with Saponin adjuvanted toxoid Group | Preparation used/route | Challenge* Strain/route | Nos. of birds challenged | Survivors on different post challenge days 2 | 5 | 10 | 15 | 20 | Protection % |
|---|---|---|---|---|---|---|---|---|---|
| A | Toxoid + Saponin (s/c) | S.W. | 8 | 8 | 8 | 8 | 8 | 8 | 100 |
| | | S.G. | 8 | 8 | 8 | 8 | 8 | 8 | 100 |
| B | Saponin (s/c) | S.W. | 8 | 8 | 6 | 3 | 2 | — | 0 |
| | | S.G. | 8 | 8 | 7 | 2 | 1 | 1 | 12.5 |
| C | PBS (control) (s/c) | S.W. | 8 | 8 | 5 | 4 | 1 | — | 0 |
| | | S.G. | 8 | 8 | 6 | 4 | — | — | 0 |

*Challenged on the 21st day post vaccination with 2 × $10^9$ C.F.U. of the challenge strain, Route of challenge i/p
S.W. Salmonella Weltevreden
S.G. Salmonella Gallinarum
PBS Phosphate buffer saline

TABLE 6

Humoral immune response to saponin adjuvanted toxoid

| Group | Preparation used/route | Agglutination titre (dpv) 7 | 14 | 21 | ELISA titer (dpv) 7 | 14 | 21 |
|---|---|---|---|---|---|---|---|
| A | Toxoid + Saponin (s/c) | 16 | 64 | 256 | 5.28 × $10^3$ | 6.93 × $10^3$ | 9.89 × $10^3$ |
| B | Saponin (s/c) | 0 | 2 | 2 | 1.5 × $10^1$ | 1.63 × $10^1$ | 1.99 × $10^1$ |
| C | PBS (control) (s/c) | 0 | 2 | 2 | 1.06 × $10^1$ | 1.11 × $10^1$ | 1.07 × $10^1$ |

Dpv: Days post vaccination
PBS: Phosphate buffer saline

TABLE 7

Post challenge shedding of Salmonella by birds immunized with saponin adjuvanted toxoid

| Group | Preparation used/route | Challenge* strain/route | Nos. of birds challenged | Shedders ** on different post challenge days 2 | 5 | 10 | 15 | 20 |
|---|---|---|---|---|---|---|---|---|
| A | Toxoid + Saponin (s/c) | S.W. | 8 | 0 | 1 | 0 | 0 | 0 |
| | | S.G. | 8 | 1 | 1 | 0 | 0 | 0 |
| B | Saponin (s/c) | S.W. | 8 | 6 | 4 | 2 | 2 | 0 |
| | | S.G. | 8 | 7 | 5 | 1 | 1 | 0 |
| C | PBS (control) (s/c) | S.W. | 8 | 6 | 5 | 3 | 1 | 0 |
| | | S.G. | 8 | 5 | 3 | 2 | 0 | 0 |

*Challenged on the 21st day post vaccination with 2 × $10^9$ C.F.U. of the challenge strain, Route of challenge i/p
**Detected by cloacal swab culture
S.W.: Salmonella Weltevreden
S.G.: Salmonella Gallinarum
PBS: Phosphate Buffer saline

We claim:

1. A process for the preparation of a vaccine from enterotoxin and cytotoxins isolated from Salmonella enterica subspecies for protection against Salmonellosis in poultry, comprising;

treating the said toxins with formalin in a ratio appropriate to result in lost toxicity but retained immunogenicity and incubating for 40–50 hours at 35–38° C. temperature to form a formalized toxoid, removing formalin by dialysis against phosphate buffer saline (PBS), concentrating the formalized toxoid by dialysing against polyethylene glycol, and adding immuno-potentiator selected from Freund's Complete Adjuvant (FCA) or Vitamin E or Saponin, to said concentrated formalized toxoids to get the desired vaccine.

2. A process as claimed in claim 1 wherein said enterotoxin and cytotoxins is isolated from a single strain of S. Weltevreden, *S. typhinuium* and *S. gallinarum.*

3. A process as claimed in claim 2 wherein said enterotoxin and cytotoxins is isolated from a single strain of S. Weltevreden.

4. A process as claimed in claim 1 wherein the concentration of formalin is 0.1–0.25%.

5. A process as claimed in claim 4 wherein the concentration of formalin is 0.2%.

6. A process as claimed in claim 1 wherein the ratio of the concentration of formalin with toxin is 1:1.

7. A process as claimed in claim 1 wherein the pH concentration of phosphate buffer saline (PBS) is 7.4.

8. A process as claimed in claim 1 wherein the concentration of said formalized toxoid is 0.1 mg/ml.

9. A process as claimed in claim 1 wherein 0.5–1 ml of said FCA is added per ml of said concentrated toxoid.

10. A process as claimed in claim 9 wherein 1 ml of said FCA is added per ml of said concentrated toxoid.

11. A process as claimed in claim 1 wherein 90–110 international units (IU) of said vitamin E is added per ml of the said concentrated toxoid.

12. A process as claimed in claim 11 wherein 100 IU of said vitamin E is added per ml of the said concentrated toxoid.

13. A process as claimed in claim 1 wherein 50–150 μg of said saponin is added per ml of the said concentrated toxoid.

14. A process as claimed in claim 13 wherein 100 μg of said saponin is added per ml of the said concentrated toxoid.

15. A Salmonella vaccine obtainable by the process as claimed in claim 1 for protection against Salmonellosis in poultry.

16. The Salmonella vaccine of claim 15, wherein at least 80% of poultry administered an effective amount of said vaccine acquire sufficient protection against Salmonellosis to survive when challenged intraperitoneally with Salmonella Weltevreden or *Salmonella typhimurium* or *Salmonella gallinarum* at $2\times10^9$ CFU/bird at 15 or 21 or 30 days post vaccination.

17. The process of claim 1, wherein at least 80% of poultry administered an effective amount of said vaccine acquire sufficient protection against Salmonellosis to survive when challenged intraperitoneally with Salmonella Weltevreden or *Salmonella typhimurium* or *Salmonella gallinarum* at $2\times10^9$ CFU/bird at 15 or 21 or 30 days post vaccination.

18. The process of claim 17, wherein an effective amount of said vaccine is 1 or 2 ml of a solution comprising said formalized toxoid in a concentration of 0.1 mg/ml.

19. A process for protecting against Salmonellosis in poultry, the process comprising administering to said poultry the vaccine of claim 15.

20. The process of claim 19, wherein said vaccine administered to said poultry comprises said formalized toxoid at a concentration of 0.1 mg/ml.

21. A process for protecting against Salmonellosis in poultry, the process comprising administering to said poultry the vaccine of claim 16.

22. A Salmonella vaccine obtained by the process as claimed in claim 1 for protection against Salmonellosis in poultry.

* * * * *